United States Patent [19]

Whalen

[11] Patent Number: 5,702,911
[45] Date of Patent: Dec. 30, 1997

[54] DIAGNOSTIC TEST COMPOSITION

[75] Inventor: Robert G. Whalen, Willington, Conn.

[73] Assignee: Chek-Med Systems, Inc., Camp Hill, Pa.

[21] Appl. No.: 698,384

[22] Filed: Aug. 15, 1996

[51] Int. Cl.⁶ .............................. C12Q 1/58; C12Q 1/28; C12Q 1/04
[52] U.S. Cl. .............................. 435/12; 435/28; 435/34; 435/29; 435/7.2; 435/7.32; 423/582; 423/584; 436/63; 514/925; 514/926
[58] Field of Search ........................... 435/12, 28, 34, 435/29, 7.2, 7.32; 423/582, 584; 436/63; 514/925, 926

[56] References Cited

U.S. PATENT DOCUMENTS

| | | | |
|---|---|---|---|
| 3,395,082 | 7/1968 | Mast | 195/103.5 |
| 3,461,036 | 8/1969 | Horcil | 435/12 |
| 4,101,382 | 7/1978 | Chang | 195/103.5 |
| 4,282,316 | 8/1981 | Modrovich | 435/12 |
| 4,748,113 | 5/1988 | Marshall | 435/12 |
| 5,258,178 | 11/1993 | Cordle et al. | 424/85.8 |
| 5,260,057 | 11/1993 | Cordle et al. | 424/85.8 |
| 5,304,540 | 4/1994 | Blackburn et al. | 514/2 |
| 5,314,804 | 5/1994 | Boguslaski et al. | 435/12 |
| 5,439,801 | 8/1995 | Jackson | 435/12 |
| 5,459,041 | 10/1995 | Blaster et al. | 435/12 |
| 5,498,528 | 3/1996 | King | 435/34 |

OTHER PUBLICATIONS

"Diagnosis of Helicobacter Pylori Infection", Kyle E. Brown, M.D. & David A. Peura, M.D., Helicobacter Pylori Infection, vol. 22, No. 1, Mar. 1993, pp. 105–115.

*Annals of Internal Medicine*, David Y. Graham, 1192; 116 No. 9 (Oct. 1, 1993).

Difco Manual 9th ED., Difco Laboratories, Detroit, MI, 1952. (Month not available).

*The Lancet*, B.J. Marshall, Jun. 22, 1985.

Derwent Publication C–86–141647 (1986) Month not available.

Derwent Publication D–84–128710 (1985) Month not available.

Derwent Publication C–90–068529 (1990) Copy not included.

*Helicobacter pylori in Peptic Ulceration and Gastritis* Barry J. Marshall, Richard W. McCallum & Richard L. Guerraut, Blackwell Scientific Publication, Boston, MA, USA, Chapters 4, 7 and 12. (1992). Month not available.

"Marshall's Hunch", *The New Yorker Magazine*, pp. 64–72 Sep. 20, 1993.

"The Doctor Who Wouldn't Accept No", *Readers Digest Magazine*, pp. 120–124, Oct., 1993.

*Primary Examiner*—Louise Leary
*Attorney, Agent, or Firm*—Eugene Chovanes

[57] ABSTRACT

The present invention relates to an improved test composition for the diagnosis of gastric ulcers, duodenal ulcers, gastritis, gastric lymphoma and gastric carcinoma by the detection of the bacteria *Helicobacter pylori* and the enzyme catalase associated with such conditions. The new test composition differs from the prior art agar compositions in being an aqueous solution containing hydrogen peroxide, urea, monobasic sodium phosphate and bromthymol blue as an indicator, and in being far more rapid than the prior art test compositions.

6 Claims, No Drawings

DIAGNOSTIC TEST COMPOSITION

The present invention relates to an improved composition for diagnosing peptic ulcers, duodenal ulcers and gastric cancer, and other disorders.

BACKGROUND AND PRIOR ART

The genesis of the art was reported by Dr. B. J. Marshall in Rapid Diagnosis of *Campylobacter pylori* Associated with Gastric Diseases in The Lancet, June 22, 1985. Since that time it has been widely accepted in gastroenterology that at least gastric ulcers, duodenal ulcers, gastritis, gastric lymphoma, and gastric carcinoma are associated with the presence of *Helicobacter pylori* bacteria in the gastric lining or mucosa. Much work has been done in this field. Several diagnostic tests for *Helicobacter pylori* in gastric biopsy specimens have been suggested. Among these see Marshall U.S. Pat. No. 4,748,113 issued May 31, 1988 and Jackson U.S. Pat. No. 5,439,801, issued Aug. 8, 1995. Both of these patents describe test compositions containing urea which produces ammonia under the influence of the urease enzyme associated with the *Helicobacter pylori* bacteria. This reaction produces a rise in the pH of the test media which is detected by a color change in a suitable dye indicator in the test media. The Marshall and Jackson patents describe the prior art in detail.

While the tests for *Helicobacter pylori* to diagnose gastric disease have been successful and have been widely adopted, the art has recognized that these tests could be improved, particularly as to reducing the time required to obtain the final result.

It is a primary object of the present invention therefore, to provide test compositions for rapidly detecting the presence of *Helicobacter pylori* for diagnostic purposes.

It is another object of the present invention to detect and utilize the catalase enzyme which is also useful in diagnosing the presence of and identification of microorganisms other than *Helicobacter pylori*.

It is another object of the present invention to detect and identify *Helicobacter pylori* in the diagnosis of other diseases.

SUMMARY OF THE INVENTION

The present invention relates to a new diagnostic test composition in the form of an aqueous solution containing:

a) about 0.5% to about 6% hydrogen peroxide;

b) about 0.5% to about 2.0% urea;

c) about 0.001% to about 0.01% monobasic sodium phosphate; and d) about 0.01% to about 0.1% bromthymol blue indicator; the remainder being water.

While the detection of *Helicobacter pylori* is a primary object of the invention, the new test composition has additional utility in the detection and identification of other microorganisms of medical interest. For example, *Helicobacter pylori* and other bacteria also contain the enzyme catalase.

Catalase decomposes hydrogen peroxide ($H_2O_2$) into water and oxygen. The decomposition produces a characteristic foaming reaction as $O_2$ is released. This catalase reaction has been used as a tool to aid in microorganism identification. While numerous microbes are catalase positive, the distinction between catalase positive organisms and catalase negative organisms has been used to differentiate microbes for at least fifty years.

As in the prior art, urease decomposes urea into ammonia. Ammonia being strongly alkaline, radically increases the pH of the reaction. *Helicobacter pylori* produces more urease than other currently known bacteria. This copious production was recognized by the Marshall and Jackson patents, as noted above.

The test composition of this invention not only exploits the presence of both the urease and catalase enzymes present in the microorganism, but it also exploits the potential presence of catalase in the biopsy specimen. Since many mammalian tissues contain catalase, catalase may be present in the biopsy specimen as well as the microorganism. The effect of the catalase on the peroxide, via the foaming and resultant agitation of the test media, is to expedite the urease reaction and rapidly raise the pH level and therefore change the color of the test media.

Major improvements in the new composition include improved sensitivity and specificity of the test in a greatly reduced time frame. It appears that, in in vitro testing, sensitivity and specificity at about 5 minutes are approximately 2–3 times greater than that of the prior art. The new test is completed usually in 5 minutes whereas the prior art tests are not completed for up to 4–24 hours. The test can detect the presence of two *Helicobacter pylori* enzymes: catalase and urease. The prior art is capable of detecting only the urease.

The preferred new test composition is in a liquid formulation containing:

| Product | Approximate % of Final Composition By Weight |
|---|---|
| Hydrogen Peroxide | 1.5% |
| Bromthymol Blue | 0.03% |
| Urea | 1.5% |
| Monobasic Sodium Phosphate in this preferred composition. | 0.010–0.05% |

Hydrogen peroxide 3% or the equivalent comprises approximately half of the aqueous vehicle (final concentration of preferred composition is about 1.5%). The peroxide serves three purposes:

1) It serves as a substrate for the catalase enzymes of *Helicobacter pylori* and/or the biopsy specimens.

2) It also serves as a preservative agent and protects the test composition from microbial contamination.

3) It also serves to speed the reaction when urease is present. The foaming-bubbling reaction produced by the catalase-driven decomposition of peroxide agitates and blends the urease enzymes through the mixture, enhancing the reaction time.

Bromthymol Blue (BTB) serves as the dye indicator. The test may also be formulated with additional pH indicators such as methyl red. This test composition has an initial pH of about 4.5. If we use only the BTB indicator, the initial pKa is about 7.0. When *Helicobacter pylori* is present, the decomposition of the peroxide and the degradation of urea to ammonia raises the pH level and produces the characteristic color change from yellow to green to blue.

Urea is present to detect the urease enzyme of *Helicobacter pylori*. If urease is present, the urea is degraded to ammonia which dramatically raises the pH level.

Monobasic sodium phosphate serves as an acidifying agent. Although hydrogen peroxide is also acidic, the $NaH_2PO_4$ is necessary to maintain a pH of less than 6.0 if the peroxide totally decomposes. Thus, if a specimen producing only catalase is introduced into the new test composition, the peroxide will be converted to $H_2O$ and $O_2$ but the test will remain negative for *Helicobacter pylori*, i.e., little or no color change.

It is important to note that there is no agar in the new test composition. The new test is in the form of a liquid, not a gel. The liquid provides total surface contact with the biopsy. The enzymes diffuse more rapidly through the liquid composition than the gel compositions of the prior art.

In view of the foregoing, it will be apparent that the new test composition provides a more rapid and specific test for the presence of *Helicobacter pylori* in a test specimen of any kind.

What is claimed is:

1. An improved test composition for detecting *Helicobacter pylori* in a specimen comprising by weight:
   a) an aqueous solution containing about 0.5% to about 6% hydrogen peroxide;
   b) about 0.5% to about 2.0% urea;
   c) about 0.001% to about 0.01% monobasic sodium phosphate;
   d) about 0.01% to about 0.1% bromthymol blue indicator; and
   the remaining percent is water.

2. The test composition of claim 1 in which the aqueous solution has an initial pH of about 4.0 to about 5.2.

3. The test composition of claim 1 wherein the aqueous solution contains by weight:
   a) about 1.5% hydrogen peroxide;
   b) about 1.5% urea;
   c) about 0.01% to about 0.05% monobasic sodium phosphate;
   d) about 0.03% bromthymol blue; and the remaining percent is water.

4. The test composition of claim 1, 2, or 3 further comprising an additional indicator.

5. The test composition of claim 4 wherein the additional indicator is methyl red.

6. A test composition comprising a) an aqueous solution containing about 0.5% to about 6.0% hydrogen peroxide; b) about 0.5% to about 2.0% urea; c) about 0.001% to about 0.01% monobasic sodium phosphate; d) about 0.01% to about 0.1% bromthymol blue indicator; and the remaining percent is water that exploits the presence of catalase in a microorganism test specimen and/or a biopsy test specimen to expedite the decomposition of urea by the urease enzyme.

* * * * *